United States Patent [19]

Greenblatt

[11] Patent Number: 4,707,587

[45] Date of Patent: Nov. 17, 1987

[54] BLOOD WARMING METHOD AND APPARATUS USING GASEOUS HEAT EXCHANGE MEDIUM

[76] Inventor: Gordon M. Greenblatt, 5533 N. 3rd St., Phoenix, Ariz. 85012

[21] Appl. No.: 822,657

[22] Filed: Jan. 27, 1986

[51] Int. Cl.$^4$ .............................................. H05B 1/02
[52] U.S. Cl. .................................. 219/299; 219/506; 219/302; 219/308; 128/400; 604/113; 165/102; 165/170; 422/46
[58] Field of Search ............... 219/400, 497, 299, 494, 219/302, 501, 325, 499, 308, 506; 128/400; 604/113, 114; 422/46; 165/177, 102, 46, 100, 168-172

[56] References Cited

U.S. PATENT DOCUMENTS

| | | |
|---|---|---|
| 1,831,151 | 11/1931 | Walker . |
| 2,063,902 | 12/1936 | Beasley .................... 219/39 |
| 2,688,808 | 9/1954 | Ipsen ....................... 34/219 |
| 2,845,929 | 8/1958 | Strumia ................. 128/276 |
| 3,315,681 | 4/1967 | Poppendiek ........... 128/399 |
| 3,475,590 | 10/1969 | Pins ........................ 219/302 |
| 3,480,015 | 11/1969 | Gonzalez .............. 128/276 |
| 3,590,215 | 6/1971 | Anderson ............... 219/298 |
| 3,614,385 | 10/1971 | Borstmann ............ 219/303 |
| 4,167,663 | 9/1979 | Granzow, Jr. et al. ....... 219/506 |
| 4,177,816 | 12/1979 | Torgeson ............... 128/400 |
| 4,381,442 | 4/1983 | Guibert ................... 219/400 |
| 4,426,923 | 1/1984 | Ohata ....................... 99/468 |
| 4,512,327 | 4/1985 | Stiegler .................. 219/400 |
| 4,531,941 | 7/1985 | Zasuwa ................... 604/113 |

OTHER PUBLICATIONS

*Health Devices,* Jul. 1984, vol. 13, No. 9, pp. 191-219 "Blood Warmers".
"In-Line Blood Warming and Microfiltration Devices", *Acta anaesth. scand.* 1979, pp. 40-45, K. Linko.
*Anaesth. Intens. Care,* "A Review of Blood Warmers for Massive Transfusion", 1974, W. J. Russell pp. 110-130.

*Primary Examiner*—M. H. Paschall
*Attorney, Agent, or Firm*—Cahill, Sutton & Thomas

[57] ABSTRACT

A blood warming device circulates air as a heating medium through a heater element and heat exchangers to transfer heat from the air to chilled blood being forced through the channels in a disposable warming jacket. A temperature sensor is disposed near an outlet of the blood warming jacket. An electronic control circuit operates on the signals produced by the temperature sensor to produce a cutoff signal that immediately stops the flow of heated air through the heat exchanger if the sensed blood temperature exceeds a predetermined level. The low heat capacity of the air is sufficiently low that no overheating of blood in the blood warming jacket occurs even if the blood flow is interrupted so that blood remains stationary in the blood warming jacket. The disposable warming jacket inclues a plurality of parallel blood paths, resulting in a high flow rate of heated blood. Blood output from one section of a warming jacket can be input to the inlet of another section to further raise the temperature thereof.

32 Claims, 20 Drawing Figures

BLOOD WARMING METHOD AND APPARATUS USING GASEOUS HEAT EXCHANGE MEDIUM

BACKGROUND OF THE INVENTION

The invention relates to devices and methods for warming chilled blood delivered from a disposable storage bag in a pressure infusion device to near normal body temperature before infusion into a patient; the invention relates more particularly to improvements in such blood warming devices to prevent overheating of blood in the blood warming jacket in the event that movement of blood in the blood warming jacket is slowed or stopped.

It is well known that when massive transfusions of blood are required, the blood, which is normally chilled in disposable plastic storage bags at temperatures of about 4° Centigrade must first be warmed to near normal body temperature in order to avoid hypothermia and other complications. A variety of prior blood warming devices have been proposed for receiving chilled blood from pressure infusion devices, heating the blood as it is forced through a tube from the pressure infusion device, before the heated blood is infused by means of a catheter or needle into a patient. Some of the prior blood warming devices consist of simply passing a coiled tube through which the chilled blood passes through a heated water bath before the blood is forced into the infusion catheter. Other prior devices include a blood warming jacket that is inserted into a blood warming device. The blood is forced into an inlet of the blood warming jacket and through a thin channel in the disposable blood warming jacket. An outlet of the blood warming jacket is connected to a tube to conduct the warmed blood into the infusion catheter.

It is generally accepted that blood should not be heated above 42° Centigrade before being infused into a patient's body. All prior known prior blood warming devices utilize water or electrical heating elements to effectuate thermal transfer of heat to the blood.

However, both water and the metal of electrical heating elements have high thermal mass, i.e., high thermal heat capacity. Such high thermal mass may cause "temperature overshoot" of the blood being warmed when the movement of such blood through the heating jacket or coiled tube is halted (for example by temporary loss of pressure in the pressure infusion device) because a large amount of heat contained in the water or electrical heating element continues to be transferred into the stationary blood.

The prior blood warming devices have been unable to achieve the high infusion rates that are necessary in certain instances when massive transfusions are required, heat the chilled blood to the necessary minimum temperature during such massive transfusions, and still avoid the risk of overheating a portion of the blood in the event of a temporary slowing or halting of the flow of blood through the blood warming device.

It is known that in certain emergency circumstances, massive blood transfusion rates of up to 1000 milliliters per minute may be required. It would be desirable that a blood warming device be able to precisely heat chilled blood to 40° C. for infusion rates as low as 200 milliliters per minute to infusion rates as high as about 1000 milliliters per minute, without any danger of any blood cells being heated above 42° Centigrade, even in the event of a malfunction that halts flow of blood in the blood warming device.

A decrease in a patient's body temperature to a level below about 35° Centigrade may seriously jeopardize the patient's chance of survival. One risk is that of increasing the likelihood of ventricular fibrillation.

Another risk is that of imparing the ability of the patient's body to withstand blood loss. The various risks of hypothermia are described in detail in "A Review of Blood Warmers for Massive Transfusion", W. J. Russell, "Anesthesia and Intensive Care", Volume II, No. 2, May 1974, page 109, and in "Blood Warmers", Health Devices, Volume 13, No. 9, July 1984, both of which are incorporated herein by reference. U.S. Pat. No. 3,614,385 discloses a blood warming device using a liquid heating medium. U.S. Pat. Nos. 2,063,902, 3,315,681, 3,475,590, and 3,590,215 disclose blood warming devices that use dry heating plates or elements to conduct heat directly to the blood. Various prior patents, such as U.S. Pat. No. 4,426,923, disclose use of heated air to warm substances such as food.

The above July, 1984 "Health Devices" article states, "As the technology stands now, there is much room for improved warming capacity." As indicated above, there are occassions when massive transfusion rates much greater than 160 milliliters per minute rate (presently accepted as a maximum "massive" infusion rate) are required in order to save the life of a patient.

No known prior blood warming device is capable of safely raising the temperature of chilled blood up to at least 40° Centigrade at flow rates as high as one liter per minute, which in some cases would be desirable. As several of the above articles indicate, there is a considerable risk in infusing blood into a patient if any of the blood cells have been heated to above approximately 42° Centigrade. Hemolysis of the red blood vessels may occur, leading to poor oxygen transport in the blood, kidney failure, and increased potassium levels that can cause cardiac irregularity.

Thus, despite the advances in blood warming devices over the last decade to prevent hypothermia and other complications during massive transfusions, there is still a clearly unmet need for a greatly improved, inexpensive, easily maintained, easily operated, safe blood warming device capable of heating massive transfusions of chilled blood without appreciable risk of overheating any of the transfused blood.

SUMMARY OF THE INVENTION

Accordingly, it is an object of the invention to provide an apparatus and technique for warming blood uniformly to a predetermined temperature while avoiding overheating of any portion of the blood as a result of high thermal mass of a heating medium.

It is another object of the invention to provide a blood warming apparatus and technique that can accurately, uniformly heat blood in a blood warming jacket to a predetermined temperature at a wide range of infusion rates, from very low to very high infusion rates.

Briefly described, and in accordance with one embodiment thereof, the invention provides a blood warming device that warms blood passing through a blood warming jacket by circulating a gaseous heat carrying medium through a heating element and a heat exchanger that thermally contacts the blood warming jacket. In a described embodiment of the invention, a sterile blood warming jacket composed of two thin, laminated layers of plastic and high thermal conductivity aluminum defines at least one serpentine blood path between the laminated plastic-aluminum layers leading from a blood inlet connector to a blood outlet connector. Stiffening members support the outer edges of the blood warming jacket to allow it to be conveniently inserted between heated walls that form a deep, narrow, blood jacket receiving channel of the blood warming apparatus. The heated walls of the blood jacket receiving channel are thermally contacted by the heat exchangers through which the heated air is recirculated. Pressurized chilled blood fed into the blood inlet from a pressure infusion device expands the serpentine path in the blood warming jacket, causing the walls of the blood warming jacket to tightly contact the heated walls of the blood jacket receiving channel. A temperature sensitive sensor placed in the blood warming jacket near a blood outlet thereof produces a signal that is processed upon by a control circuit to regulate the amount of power applied to the heating element and/or an electric blower that recirculates the gaseous medium, which in the described embodiments of the invention is air. In the described embodiment of the invention, the blood warming device includes an upper section having two deep, parallel pairs of two blood jacket receiving channels, each for receiving a separate blood warming jacket. Each blood warming jacket includes two separate sections, each section having a plurality of parallel-connected serpentine blood paths therein, each section of each blood warming jacket having a separate blood inlet and blood outlet, the two sections being connected by an upper web to form a saddlebag-like structure. A stiff plastic frame maintains each of the sections in a rectangular configuration to effectuate convenient insertion of the two sections into a pair of the blood jacket receiving channels. A centered handle is provided in the center of the web connecting the two sections. Each such blood warming jacket thus can be easily inserted into and removed from the blood warming device before and after pressurized blood is applied to the blood warming jacket. The two sections of each blood warming jacket can be connected in series or parallel relationship to each other by appropriately connecting the blood inlets and outlets of the two sections by suitable tubing. This configuration gives a choice of one to four transits of blood through the blood warming device, depending on the anticipated rate of blood infusion. The passages of blood through multiple sections of the warming jackets allows the heating device to raise the blood to the desired temperature at high flow rates. The four sections of the two blood warming jackets that can be inserted into the described blood warming device then can be considered to be one to four blood warming jackets that can be connected in series or parallel relationship depending on the needed infusion rate. The blood warming device of the present invention includes a detachable lower section that can be removed to allow convenient cleaning of the upper section of the blood warming apparatus. The lower section of the blood warming apparatus contains control circuitry, a pair of electrical blowers, and a pair of heating elements. The device provides a digital read out of blood temperature at a chilled blood inlet and warmed blood outlet of one or more of the sections of the two blood warming jackets and also provides a digital read out of the temperature at the air inlet and outlet of the heat exchangers. The blood warming device can be conveniently clamped on a standard IV pole along with a commercially available pressure infusion device. The determination of the heater temperatures and the air flow rates in the blood warming device can be made on the basis of blood outlet temperatures of the blood warming jacket above or on the basis of both blood outlet temperatures and blood inlet temperatures. In one described embodiment, a microprocessor reads blood inlet, blood outlet, air inlet, and air outlet temperatures and, on the basis of such readings, refers to stored empirically obtained data to determine the air flow rates and the heating element temperatures.

DESCRIPTION OF THE INVENTION

Figures 1, 3, 5, 6:
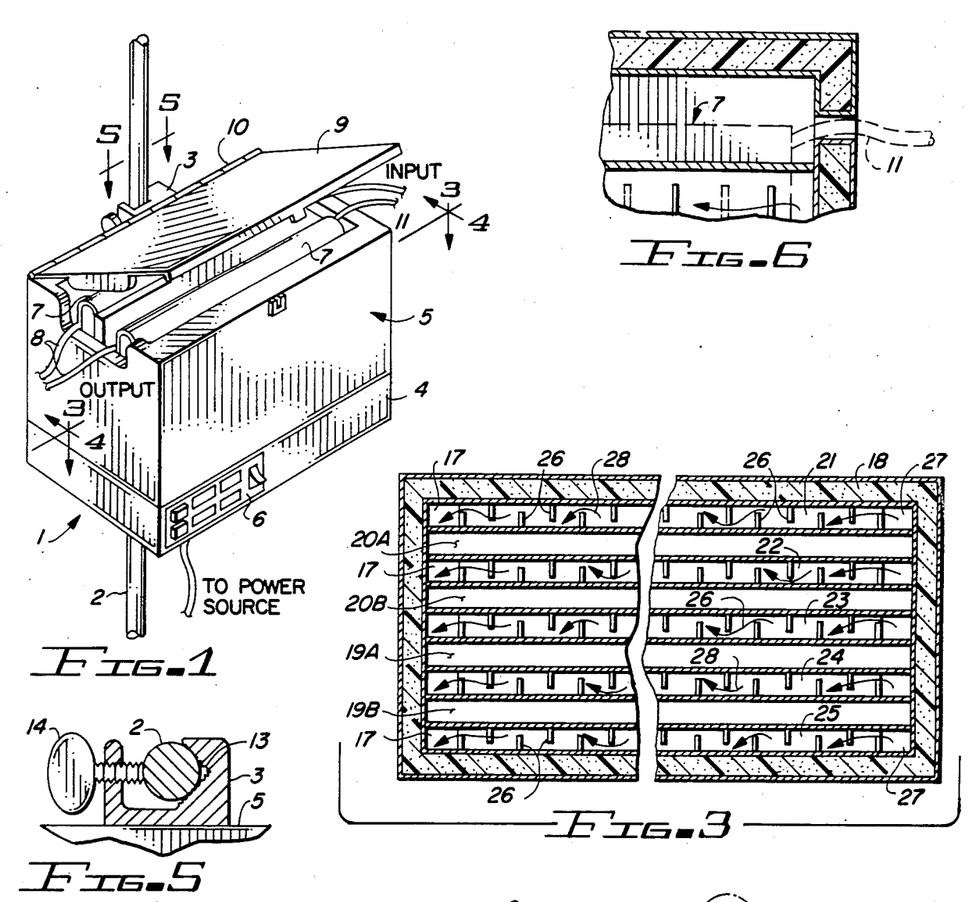
FIG. 1 is a perspective view of the blood warming apparatus of the present invention.
FIG. 3 is a section view along section line 3—3 of FIG. 1.
FIG. 5 is a section view along section line 5—5 of FIG. 1.
FIG. 6 is an enlarged view of the detail 6 of FIG. 4.

Referring now to the drawings, especially FIG. 1, blood warming device 1 includes a removable lower section 4 that is connected to an upper section 5. Upper section 5 contains four blood jacket receiving channels into which separate sections of two plastic blood warming jackets 7 are inserted. A cover 9 is connected to the back, upper edge of upper section 5 by means of a hinge 10. Cover 9 normally is closed after one or two blood warming jackets 7 have been inserted into the respective blood jacket receiving channels. Each blood warming jacket 7 has an input tube 11 for receiving chilled blood from a pressure infusion device, such as the one described in U.S. Pat. No. 4,539,005, issued Sept. 3, 1985, entitled "BLOOD INFUSION APPARATUS AND METHOD". Each blood warming jacket also includes an outlet tube 8 for supplying warmed blood to an infusion catheter or needle. The back wall of blood infusion device 1 is connected by a clamp 3 to a standard IV (intravenous) pole 2, to which a pressure infusion device ordinarily also would be attached. The clamp 3 includes a V groove 13 against which the IV tube 2 is seated, and a thumb screw 14 that tightens the clamp 3 to the IV pole 2 as shown in FIG. 5.

Figure 2:
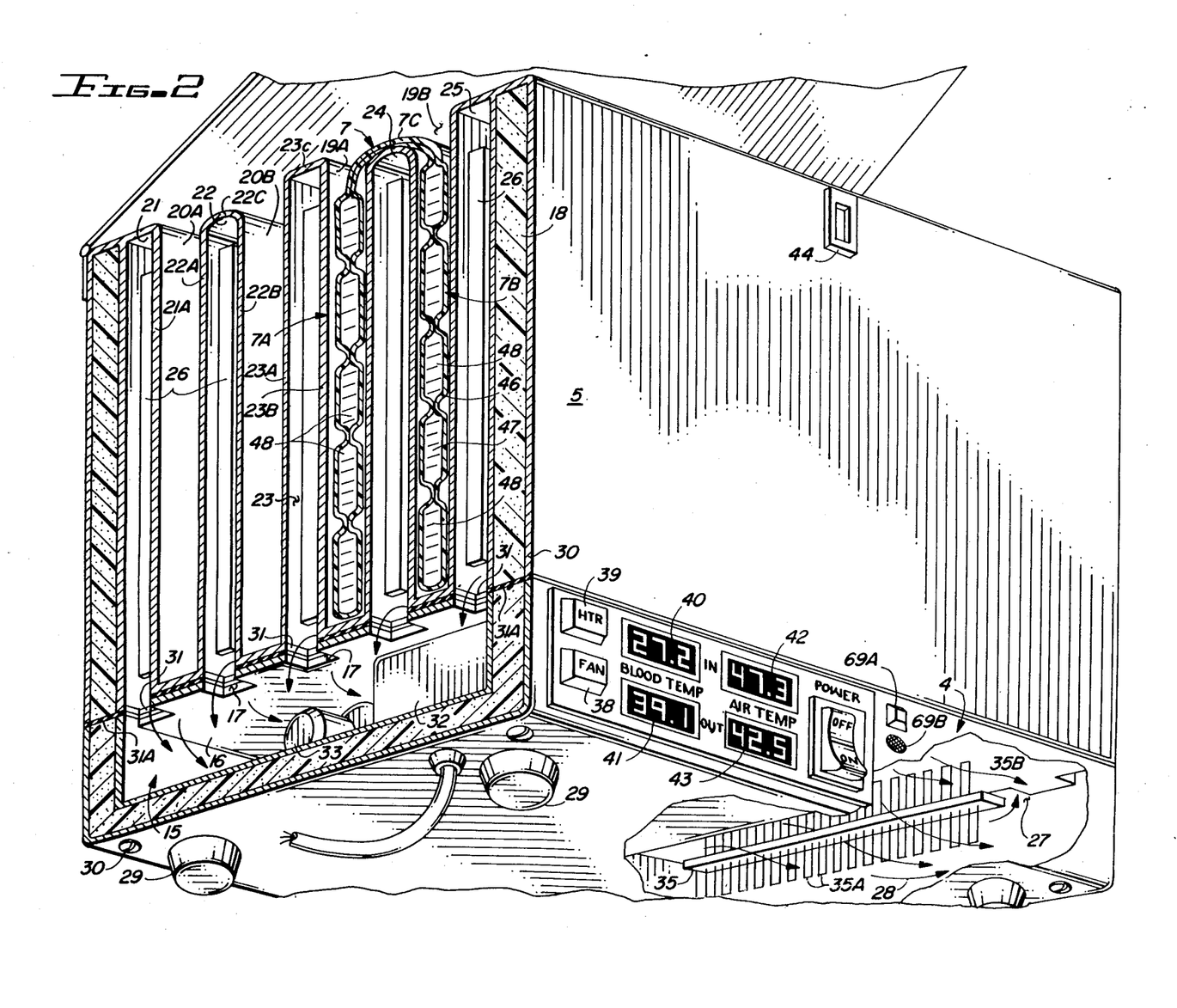
FIG. 2 is a partial perspective cutaway illustration of the blood warming apparatus of FIG. 1.

As better seen in FIG. 2, upper section 5 includes five warm air passages 21, 22, 23, 24, and 25. The outer warm air passages 21 and 25 are bounded by insulation 18 disposed between the outer walls of passages 21 and 25 and the outer housing of upper section 5.

Blood warming jacket receiving channels 19A and 19B receive opposite sections of a blood warming jacket of the present invention. Blood warming jacket channel 19A is disposed between warm air channel 23 and warm air channel 25. Blood warming jacket channel 20A is disposed between warm air channels 21 and 22. Blood warming jacket channel 20B is disposed between warm air channels 22 and 23. In FIG. 2, jacket receiving channel 20A and 20B are empty, but, if desired, a blood warming jacket 7 could be inserted therein.

Figure 4:
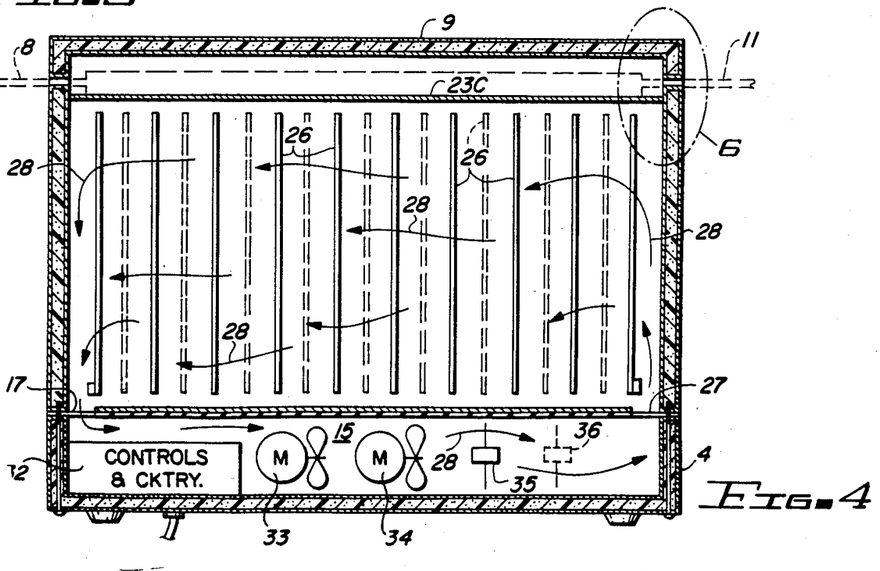
FIG. 4 is a section view along section line 4—4 of FIG. 1.

Each of the warm air channels 21-25 has a plurality of heat exchanging fins 26 disposed therein, as best seen in FIGS. 3 and 4. The fins 26 are thermally conductive, and are disposed so as to efficiently transfer heat from warm air passing through channels 21-25 in the direction of arrows 28 to the vertical walls of channels 21-25. The vertical walls of channels 21-25 are composed of material having high thermal conductivity, such as high thermal conductivity aluminum.

Figures 2A, 16:
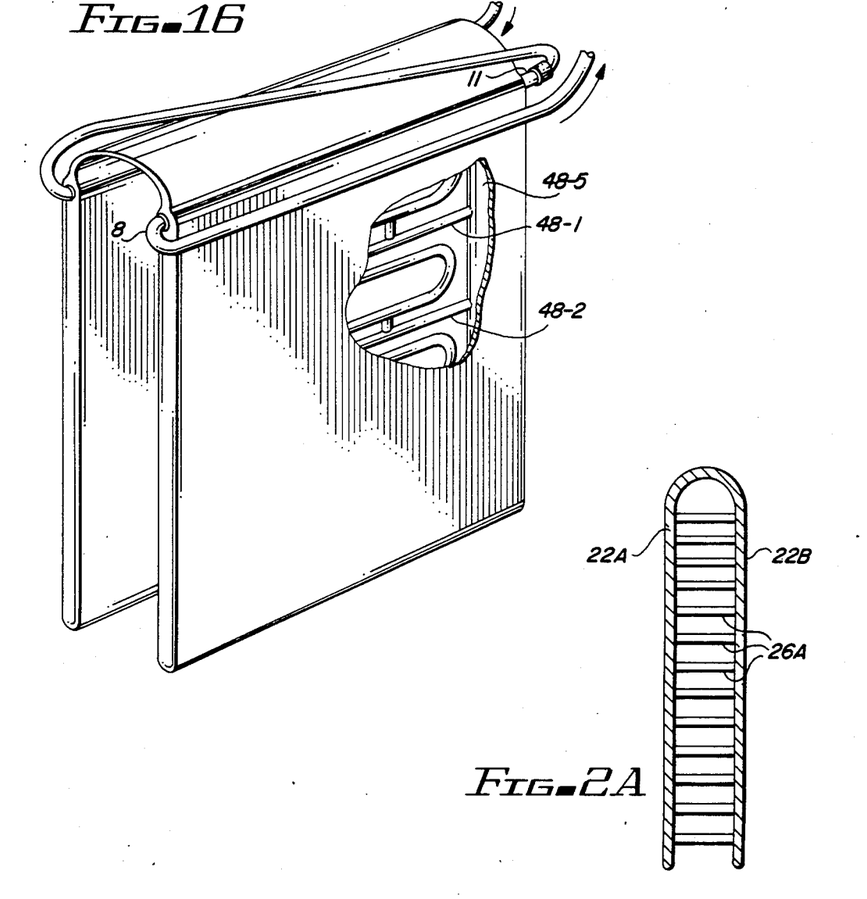
FIG. 2A is a partial section view of a warm air channel of FIG. 2 wherein the heat exchanging fins are disposed parallel to the flow of the heated air.
FIG. 16 is a perspective diagram illustrating series connection of the two sections of the blood warming jacket of the present invention.

Heat exchanging fins 26 can be alternately disposed on opposite walls of each of the warm air channels 21-25, as shown in FIGS. 3 and 4, if increasing the air turbulence in those channels is needed to increase the efficiency of conducting heat from the warm air to the walls of the warm air channels. Alternately, the fins 26 can be closely spaced parallel, horizontal fins that extend across and thermally contact both vertical walls of each of the warm air channels 21-25, as indicated by reference numeral 26A in FIG. 2A. It has not yet been determined which fin configuration will lead to optimum performance.

Upper section 5 has a solid bottom 31. A sealing gasket 31A is disposed between the bottom surface of floor 31 and the vertical walls of lower section 4.

An opening in floor 31 is provided at the end of each of the warm air inner channels 21-25. The opening on the right end of each warm air channel is designated by reference numeral 17. Each opening 17 allows warm air 28 to flow into the cavity 15 enclosed by lower section 4. The opening at the right hand of each warm air channel is designated by reference numeral 27, and allows air 28 that has been heated by heating element(s) 35 to re-enter the right-hand end of each of the each of the warm air channels 21-25.

Figure 17:
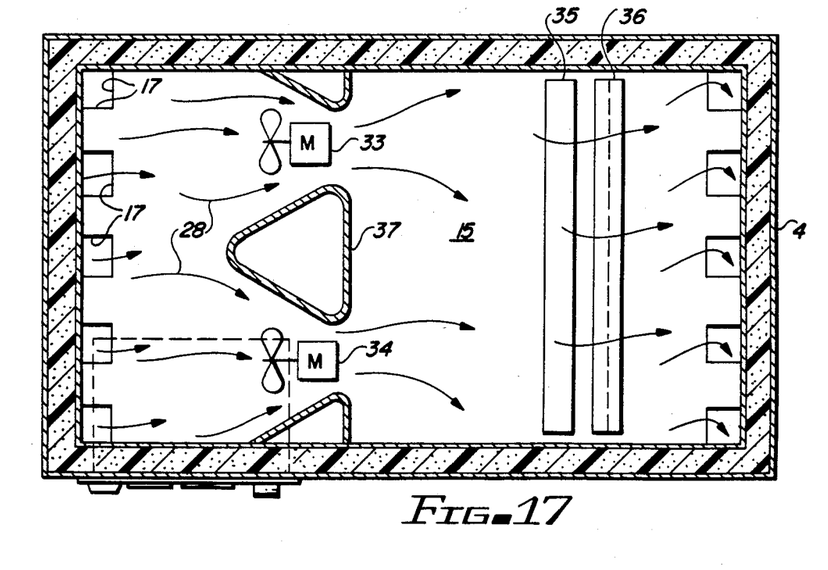
FIG. 17 is a schematic view illustrating a placement of the electrical blowers and heating elements in the lower section of the blood warming apparatus shown in FIG. 2.
Figure 18:
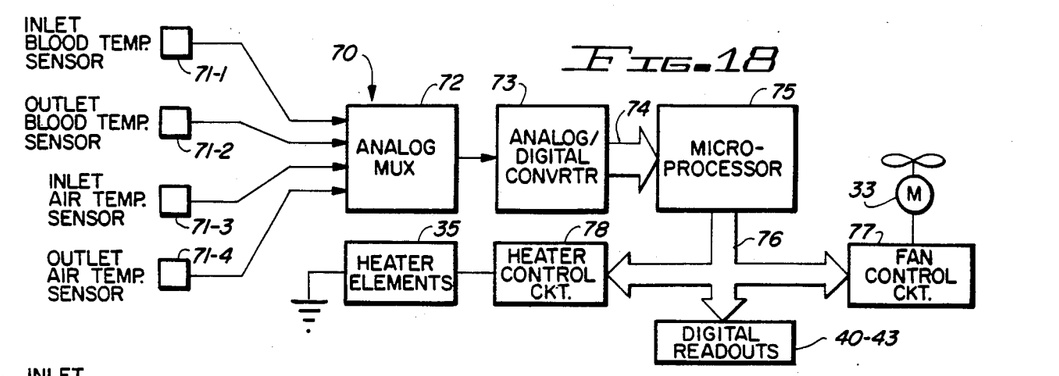
FIG. 18 is a block diagram of a control circuit for the blood warming device of the invention.
Figure 19:
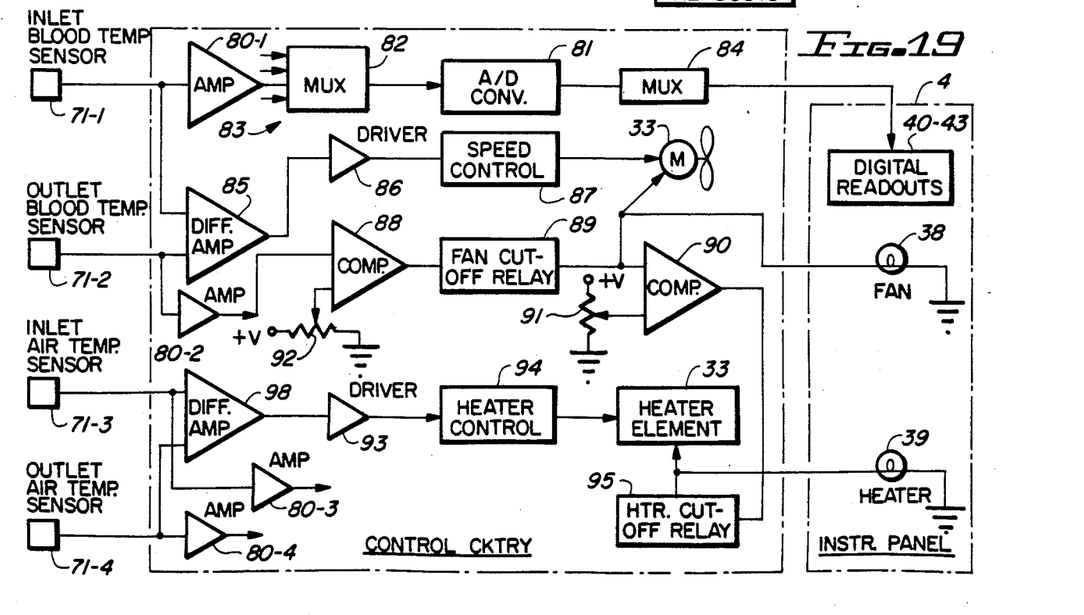
FIG. 19 is a block diagram illustrating an alternate control circuit for the blood warmer of the present invention.

As best seen in FIG. 4, a pair of electric blowers 33 and 34 is disposed in the path of recirculating air 28. FIG. 17 shows a plan view of a more practical placement of blowers 33 and 34 on opposite sides of a center baffle 37. If desired, a second heating element 36 can be positioned in cavity 15 as indicated in FIG. 17. Control circuitry 32 having the general configurations shown in FIG. 18 or 19 is housed in a corner of cavity 15 and controls the temperature of heating elements 35 and 36 and the speed of the motors of blowers 33 and 34. Those skilled in the art will appreciate that redundancy of both the electric blower and the electrical heating element is highly desirable in a blood warmer, so that the blood warming function can be continued despite a failure of one heating element or one electrical blower.

The bottom surface of lower section 4 has four foot pads 29 so that the device can be rested on a table top, if desired. Lower section 4 is detachable from upper section 5 by means of four screws 30, as seen in FIG. 2. Detachability of lower section 4 allows convenient periodic cleaning of upper section 5, and also allows convenient access to the circuitry 32, the electric blowers, and the heating elements.

Typical dimensions for the height, length, and width of each of the blood warming jacket receiving recesses 19A, 19B, 20A and 20B are about 12 inches long by 10 inches high by one-sixteenth of an inch thick.

As subsequently explained in more detail, a display panel integral with lower section 4 includes a digital read out 40 indicating the temperature of chilled blood supplied from a pressure infusion device to one of the blood jackets inserted in the upper section 5. Digital read out 41 indicates the temperature of the blood after it has been warmed. As subsequently explained, and in accordance with one aspect of the invention, blood warming jacket shown in FIG. 10 has a temperature sensor 71-1 that senses the temperature of the incoming chilled blood via inlet tube 11. The blood warming jacket also includes a blood outlet temperature sensor 71-2 that senses the temperature of the blood after it has passed through the serpentine channels (FIG. 10) of blood warming jacket 7 and flows through warm blood outlet tube to an infusion catheter.

The display panel also includes a digital readout 42 that indicates the temperature of air flowing through openings 27 into the upstream end of each of the warm air channels 21-25. Digital read out 43 indicates the outlet air temperature of the air after it has passed through the warm air channels 21 and has transferred a portion of its heat to the lines 26 and the thermally conductive walls of the warm air channels to the blood warming jackets inserted into the recesses 19A, 19B, 20A and 20B. The light 39 indicates when the heater elements 35 and 36 are on. A "fan" light 38 indicates when either of the blowers 33 or 34 are on. Alarm light 69A indicates the occurence of an unacceptably high outlet blood temperature or high outlet air temperature; a corresponding audible buzzer 69B emits a warning sound under the same circumstances. A more complex display that shows the temperature of blood at the inlet and outlet of each of the four sections of the two inserted blood warming jackets could be provided.

Figures 10, 11, 14, 15:
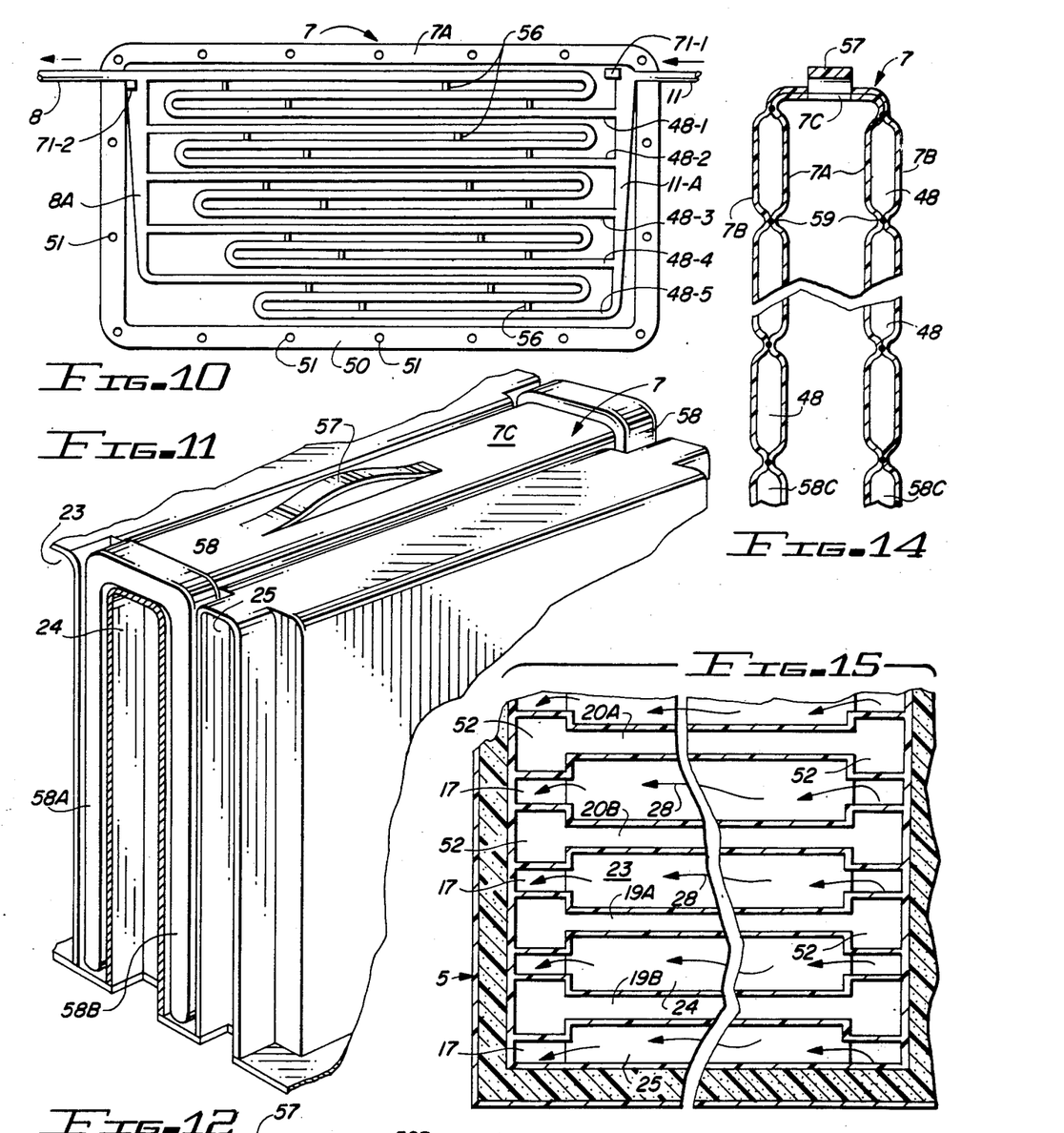
FIG. 10 is a side elevational view of a blood warming jacket of the present invention.
FIG. 11 is a partial perspective view illustrating a different blood warming jacket having an integral rectangular support frame.
FIG. 14 is a section view along section line 14—14 of FIG. 12.
FIG. 15 is a partial top section view of the embodiment of the blood warming device shown in FIG. 11, wherein each of the blood jacket receiving channels has an enlarged end section for guiding the vertical frame members of the blood jacket of FIG. 12.

Next, the configuration of a blood warming jacket 7 of the present invention will be described, with reference to FIGS. 2, 7 to 14 and 16. The basic construction of blood warming jacket 7 is best shown in FIG. 2, wherein it can be seen that blood warming jacket 7 includes two sections 7A and 7B connected by a web 7C. An elevational side view of blood warming jacket 7 is shown in FIG. 10. The construction of blood warming jacket 7 is formed by thermal welding of selected portions of two thin, flexible laminated high thermal conductivity aluminum and plastic panels 46 and 47 to form the serpentine channels as illustrated in FIG. 10. The serpentine channels are designated by reference numerals 48 in FIG. 2.

In FIG. 10, it can be seen that the chilled blood inlet tube 11, having an inside diameter of at least 5 millimeters, feeds a tapered manifold arm 11A from which five parallel, equal length, equal blood flow resistance serpentine channels 48-1, 48-2, 48-3, 48-4, and 48-5 (collectively referred to by reference numeral 48) are fed so that the blood transit times through each of the channels are equal. Each of the serpentine channels 48 passes back and forth across the sections of the blood warming jacket and feeds into a tapered warm blood manifold arm 8A, which feeds warmed blood into the outlet tube 8, which also has an inside diameter of at least 5 millimeters. The taper of the manifold arms 8 and 8A are selected to ensure equal transit times for all blood passing through the blood warming jacket.

In order to promote turbulence of the blood passing through each of the serpentine paths, so that the blood is uniformly heated by thermal conduction from the heated walls of the jacket receiving channels 19A, 19B, etc. and the thin plastic walls of the blood warming jacket, two or three short, small diameter cross paths 56 are provided in each horizontal pass of each serpentine path. This is a known technique in certain prior blood warming jackets of the type that are "dry heated" by electrically heated contacting plates.

Typically, the thickness of the plastic and aluminum laminate, which might be composed of polyvinyl chloride and high thermal conductivity aluminum material, is about 10 mils. The width of each of the serpentine paths in the vertical direction as shown in FIG. 10 can be about three-eighths of an inch. The thickness, in the horizontal direction, as shown in FIG. 2, in each of the blood passages 48 of the various sections of the blood warming jackets, when they are expanded by the pressure of blood being forced into inlet of the blood warming jacket by a pressurized infuser, is about three thirty-seconds of an inch.

When the pressurized chilled blood is fed into the blood warming jackets, each of the blood warming channels 48 expands, as indicated in FIG. 2, so that the walls of the serpentine channels press tightly against the heated walls of the blood warming jacket receiving channels 19A, 19B, etc.

The thermal welds that define the serpentine channels 48 are indicated by reference numeral 59 in FIG. 14.

Figures 7, 8, 9:
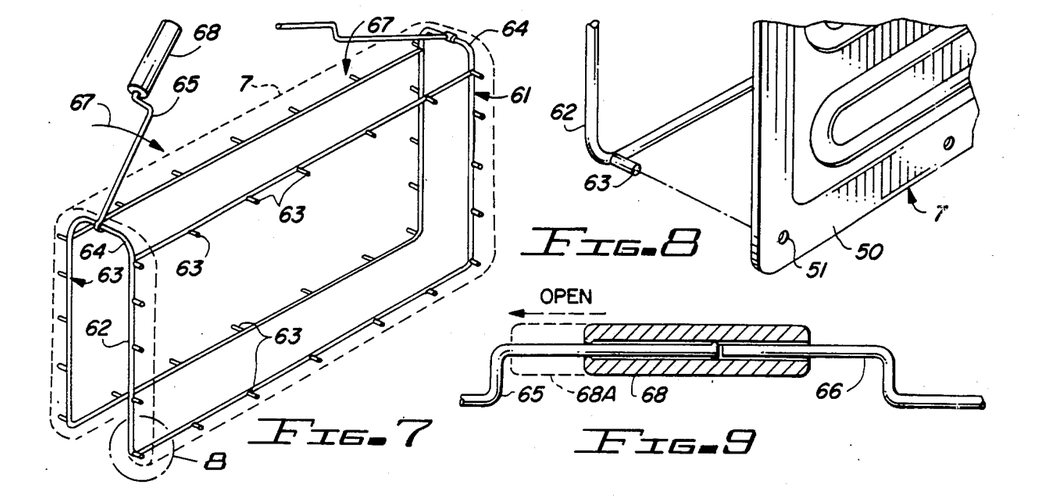
FIG. 7 is a perspective view of a support frame for a blood warming jacket frame of one embodiment of the invention.
FIG. 8 is an enlarged view of detail 8 of FIG. 7.
FIG. 9 is an elevational section view of the handle of the frame of FIG. 7.

In order to effectuate rapid, convenient insertion of the "saddle bag" configuration of blood warming jacket 7, it is necessary to provide a rigid peripheral stiffening member or frame to stretch the flexible sections 7A and 7B of blood warming jacket 7 in order to prevent the lower portions of the sections 7A and 7B from collapsing as an operator attempts to insert them into the respective jacket receiving channels. One approach for achieving this objective is to provide a flexible flange 50 around the periphery of each of sections 7A and 7B as shown in FIG. 10. A stiff wire frame 61, shown in FIGS. 7-9, is provided to peripherally support the blood warming jacket by means of flange 50. A plurality of spaced holes 51 are provided in flange 50 for receiving prongs 63 of wire frame 61, which includes two separate rectangular wire frames, the upper portion of each being connected by a member 64 to the upper portion of the other. A handle mechanism includes arms 65 and 66, which are hinged to the members 64, and swing upward to allow an unused disposable blood warming jacket 7 of the type shown in FIG. 10 to be mounted on the wire frames. The two handle members 65 are then closed downward in the direction of arrows 67, and a slidable handle latch 68 is moved from the configuration indicated by dotted line 68A, in FIG. 9 to the configuration shown by the solid line 68 so that members 65 and 66 are rigidly engaged. The mounted blood warming jackets 7 then can be very easily inserted into the jacket receiving channels such as 19A and 19B of blood warming device 1.

Figure 12:
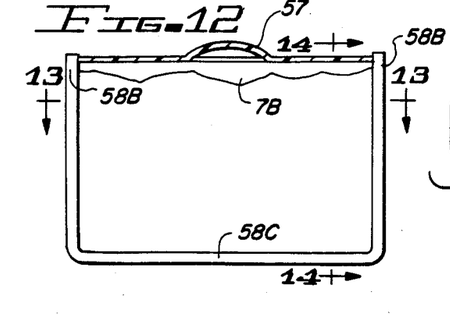
FIG. 12 is a partial side elevational view illustrating a plastic peripheral frame of the blood warming jacket of FIG. 11.
Figure 13:
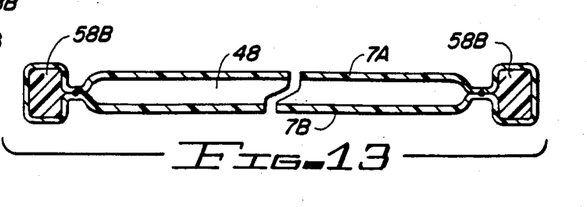
FIG. 13 is a section view along section line 13—13 of FIG. 12.

FIGS. 11-14 illustrate an alternate, and presently preferred, structure for stiffening the periphery of the sections 7A and 7B of the blood warming jacket 7. Stiff plastic members are laminated into the structure of the blood warming jackets 7 at the time they are manufactured. Reference numerals 58 in FIG. 11 illustrate U-shaped plastic end members. FIG. 12 shows a section view of this construction, wherein reference numeral 58B designates the "laminated in" vertical end members, and reference numeral 58C designates a thinner "laminated in" bottom plastic member. FIG. 13 shows that the end members 58B are slightly wider than the serpentine channels 48. FIG. 15 shows enlarged end sections 52 of the jacket receiving channels 19A, 19B, 20A, 20B for receiving and guiding the stiff end members 58B and effectuating smooth insertion of the blood warming jackets into the blood warming device. FIG. 14 illustrates the configuration of the stiff lower plastic member 58C, which is narrow enough to fit into the main portion of jacket receiving channels 19A, 19B, etc.

A handle 57 is formed in the web 7C connecting the sections 7A and 7B of the blood warming jacket, by simply making two parallel slits in the web material, as shown in FIG. 11.

Various control circuits can be utilized in block 32 of FIG. 1. One type of control circuit is illustrated in the block diagram of FIG. 18, wherein each of the inlet blood sensors 71-1 (there may be more than one) is fed (after suitable amplification) into an analog multiplexer 72. Similarly, outlet blood temperature sensor 71-2, the inlet air temperature sensor 71-3, and the outlet air temperature sensor 71-4 also are fed as inputs into analog multiplexer 72. Analog signals produced by the various temperature sensors are sequentially multiplexed through analog multiplexer 72, which would contain an appropriate amplifier, into analog-to-digital converter 73. Analog-to-digital converter 73 is operated to convert each of the amplified analog signals to a digital equivalent on digital bus 74.

The digital numbers produced on bus 74 then are read by a microprocessor 75, which then generates input signals on a bus 76 to provide continuous updating of inputs to a fan control circuit 77 and a heater control circuit 78. The signals generated by microprocessor 75 in response to the digital numbers read on bus 74 can be produced by simply referring to a stored look-up table that stores empirically determined values of the digital numbers used to set the heater control circuit, fan control circuit and digital read out displays to appropriate values. In FIG. 18, the microprocessor output bus 76 also can be connected to the digital read out devices 40-43 of FIG. 2. Fan control circuit 78 then accurately and continuously controls the speed of blower 33. Heater control circuit 78 continuously and accurately controls the current supplied to the heater elements such as 35 and 36. Any combination of sensed blood and air temperatures that could lead to overheating of any blood anywhere in any of the inserted blood jacket sections would be recognized by the microprocessor and the fans and heating elements would be immediately turned off. Those skilled in the art of microprocessor control systems can easily implement the system of FIG. 18 without undue experimentation, as each of the illustrated components is readily commercially available from a wide variety of component manufacturers, and the empirically determined values to be stored in look-up tables of the processor 75 can be easily written into a read-only memory contained in the microprocessor 75. The values of data representations of optimum fan speeds and heater element temperatures for various conditions of sensed blood inlet and blood outlet temperatures, air inlet and air outlet temperatures, and blood flow rates can be experimentally determined without undue effort by one skilled in the art. Experimental blood warming jackets would have to be constructed with distributed temperature sensors therein to obtain suitable air flow rates and heater temperatures that would not cause overheating of any blood in the blood warming jacket if the fans failed and/or the blood flow is interrupted. Such experimentation would be straightforward, and not undue, considering the large expenditures generally neded to produce similar equipment that can be approved for general use in the medical field. Initial computations of the amount of heat that must be supplied to heat blood from 4° Centigrade to 40° Centigrade at various infusion rates can be obtained from Table 1.

TABLE 1

| Blood Infusion Rate at 4° Centigrade Warmed to 40° Centigrade (ml. per min.) | Power Requirement (Blood Flow) × 0.95 × 36 × 1.1 14.3 (watts) |
|---|---|
| 150 | 395 |
| 250 | 658 |
| 350 | 921 |
| 450 | 1184 |
| 550 | 1447 |
| 650 | 1710 |
| 750 | 1973 |
| 850 | 2236 |
| 950 | 2499 |
| 1050 | 2762 |
| 1150 | 3025 |
| 1250 | 3288 |
| 1350 | 3552 |
| 1450 | 3815 |
| 1550 | 4078 |
| 1650 | 4341 |

An alternate approach to implementing control circuitry of block 32 in FIG. 2 is illustrated in FIG. 19, wherein the various temperature sensors are connected to various differential amplifiers. The difference voltages are amplified and compared to preset thresholds by means of conventional comparator circuits, which then automatically turn off the heater elements and the electric blower motors if a blood overtemperature condition or an air overtemperature condition is sensed. More specifically, each of the sensors 71-1, 71-2, 71-3, and 71-4 is amplified by a corresponding amplifier (80-1, 80-2, 80-3, 80-4, respectively) and fed into an analog multiplexer 82, the output of which is sequentially fed into an analog-to-digital converter 81 to produce a digital output that represents the temperature of the presently selected sensor. A digital multiplexer 84 operates in synchronization with analog multiplexer 82 to feed the present digital temperature representation into the digital read out devices 40-43 of FIG. 2. It should be be noted that each of four different blood warming jacket sections can be inserted into the upper section 5 of the blood warming device 1. Each section can have an inlet blood temperature sensor and an outlet blood temperature sensor therein. Suitable thermistors or thermocouples can be utilized, and where conductors from such sensors from each can be provided. FIGS. 18 and 19 only show one inlet blood temperature sensor and one outlet blood temperature sensor; additional ones can be supplied. Additional digital read out displays as shown in FIG. 2 can be provided to display the blood outlet temperatures of each of the four blood warming jacket sections.

Still referring to FIG. 19, a blood inlet temperature sensor 71-1 and blood outlet temperature sensor 71-2 are connected to the inputs of differential amplifier 85, the output of which is connected to the positive input of comparator 88 and to a driver circuit 86. The output of driver circuit 86 is connected to an input of a conventional speed control circuit 87, which controls the speed of blower 33 in accordance with the temperature difference between the inlet blood temperature sensor 71-1 and the outlet blood temperature sensor 71-2. A potentiometer 92 sets the threshold of comparator 88 so that the fan cut off relay is actuated if the outlet blood temperature exceeds 40° Centigrade. The positive input of comparator 88 is connected to the output of outlet blood temperature sensor amplifier 80-2. The output of fan cutoff relay 89 is connected to fan indicator 38, turning it off if the blower 33 is cut off by a blood outlet over temperature condition.

The output of fan cutoff relay 89 also is connected to the positive input of a conventional comparator 90, the negative input of which is connected to potentiometer 91. The output of comparator 90 is connected to a heater cutoff relay 95, so that heater element 33 is automatically turned off whenever the fan motor 33 is turned off by a blood over temperature condition. Note that the fan and heating element cutoff circuits of FIG. 19 could be used in the system of FIG. 18 as "fail-safe" features in case the microprocessor fails.

The inlet and outlet air temperature sensors 71-3 and 71-4 are connected to the negative and positive inputs of a conventional differential amplifier 98, the output of which is connected to a driver circuit 93. The output of driver circuit 93 is connected to a conventional heater control circuit 94. The output of heater control circuit 94 controls the temperature of the heater elements 33 and 34 in accordance with the outlet air temperature sensed by outlet air temperature sensor 71-4.

It should be noted that the blood warming device described above has not been actually constructed, and that the disclosure herein is of an initial design that probably will have to be refined as a result of experimentation. However, it is believed that the device can be constructed generally in accordance with the foregoing description to provide an operable device that meets the objectives of the present invention while avoiding the danger of overheating blood cells in the event of the failure of chilled blood to advance through the blood warming jackets, or in the event of a malfunction that causes overheating of the heater elements 35 and 36.

The described device provides redundancy of blower motors and heater elements so that blood warming can continue despite failure of one of the motors, and/or one of the heater elements. Automatic adjustments in the warming air flow rate and in the heating element temperature will automatically be made to compensate for the failure of one of the blowers or one of the heating elements. The heat capacity of the air in the warm air channels 21-5 is so low that even if the air is at a temperature that is substantially higher than an acceptable maximum blood temperature of about 42° Centigrade, the air will rapidly cool off without overheating the blood in the blood warming jacket. The described device also can supply warmed blood to two or more different infusion catheters.

While the invention has been described with reference to a particular embodiment thereof, those skilled in the art will be able to make various modifications to the described system without departing from the true spirit and scope of the invention. For example, separate fans and heaters could be provided for each of the fan sections of the two inserted blood warming jackets.

I claim:

1. A method of warming chilled fluid forced out of a pressure infusion device, the method comprising the steps of:
   (a) inserting a flexible disposable fluid warming jacket into a fluid warming device, the fluid warming jacket having an inlet and an outlet and a plurality of thin elongated fluid conducting paths leading from the inlet to the outlet, the fluid warming device having a narrow, deep elongated recess for receiving the fluid arming jacket, the recess being bounded by a pair of thermally conductive opposed major walls, each thermally conductive wall having a heat exchanger in thermal contact therewith;
   (b) guiding air from an outlet of an electric blower through an electric heating element to heat the air to a predetermined temperature;
   (c) guiding the heated air from the heating element through the heat exchangers to heat the major walls;
   (d) forcing chilled fluid from the pressure infusion device into the inlet of the fluid warming jacket, thereby causing the chilled fluid to be forced into the plurality of fluid conducting paths of the fluid warming jacket and causing the fluid warming paths to expand, thereby causing the fluid warming jacket to tightly contact the heated major walls of the recess, whereby fluid moving through the fluid conducting paths is heated;
   (e) guiding air from a downstream portion of the heat exhangers to an inlet of the electric blower to thereby recycle and reheat that air;
   (f) sensing the temperature of the fluid near the outlet of the fluid warming jacket; and
   (g) immediately controlling the temperature of the heating element in response to the sensed fluid temperature to rapidly correct any overtemperature condition in the fluid,
   whereby the low heat capacity of the guided, heated air is so low that corrections in the temperature of the heating element lead to immediate corresponding corrections in the temperature of the air and prevent temperature overshoot of the fluid as the fluid absorbs heat from the air during the temperature correction so that the temperature of the guided air can be be increased to allow increased flow of the fluid without danger of overheating portions of the fluid.

2. The method of claim 1 wherein the fluid is blood.

3. The method of claim 2 including controlling the speed of the electric blower in response to the sensed blood temperature.

4. The method of claim 2 including sensing the temperature of blood near the inlet of the blood sensing jacket and controlling the the temperature of the heating element in response to both the sensed inlet blood temperature and the sensed outlet blood temperature.

5. The method of claim 2 including turning off the electric blower if the sensed blood outlet temperature exceeds a predetermined level.

6. The method of claim 2 including turning off the electric blower and the electric heating element if the temperature of the blood exceeds a predetermined level.

7. The method of claim 5 wherein the predetermined level is approximately 42° Centigrade.

8. The method of claim 5 including turning off the electric heating element if the sensed outlet blood temperature exceeds a predetermined level.

9. The method of claim 2 including guiding chilled blood being forced into the inlet of the blood warming jacket through a plurality of serpentine paths in the blood warming jacket to increase the amount of blood in thermal contact with the heated major walls of the recess.

10. The method of claim 2 including inserting a plurality of blood warming jackets into the blood warming device, the blood warming device having a plurality of recesses bounded by closely spaced parallel major walls heated by transferring heat from the heated air to the heated major walls by means of heat exchangers.

11. The method of claim 10 including connecting the inlets of the plurality of blood warming jackets in parallel relationship to each other and connecting the outlets of the plurality of blood warming jackets together in parallel relationship to each other.

12. The method of claim 10 wherein the outlet of one of the blood warming jackets is connected to the inlet of another of the blood warming jackets, and the outlet of the second blood warming jacket is connected to an infusion catheter.

13. The method of claim 2 including guiding blood from the outlet of the blood warming jacket through a tube to an infusion catheter.

14. The method of claim 2 wherein the blood warming jacket is supported by a peripheral frame to facilitate insertion of the blood warming jacket into the recess of the blood warming device.

15. The method of claim 5 including operating on a signal produced by a temperature sensing element disposed in the blood warming jacket near the outlet thereof by means of an electronic control circuit to produce first and second control signals and adjusting the temperature of the heating element in response to the first control signal and turning off the blower in response to the second control signal if the temperature of the outlet blood exceeds the predetermined level.

16. The method of claim 15 including converting the signal representative of the sensed blood outlet temperature to a digital number by means of an analog-to-digital converter, operating a microprocessor to repetitively read the digital output of the analog-to-digital converter, and operating upon the digital output to produce heater control signals, and repetitively adjusting the heater temperature in response to the heater control signals.

17. The method of claim 15 including operating the microprocessor in response to the digital output to generate blower speed control signals and repetitively adjusting the speed of the blower in response to the blower speed control signals.

18. The method of claim 17 including operating the microprocessor to generate digital readout signals and producing a digital readout representative of the outlet blood temperature in response to the digital readout signals.

19. The method of claim 5 including operating on a signal produced by a temperature sensing element disposed in the blood warming jacket near the outlet thereof by means of an electronic control circuit to produce a control signal and adjusting the blower speed in response to the control signal.

20. A fluid warming device for warming chilled fluid forced out of a pressure infusion device, the fluid warming device comprising in combination:
(a) a flexible disposable fluid warming jacket having an inlet and an outlet and a plurality of thin elongated fluid conducting paths leading from the inlet to the outlet;
(b) a narrow, deep elongated recess for recess for receiving the fluid warming jacket, the recess being bounded by a pair of thermally conductive opposed major walls;
(c) heat exchanging means for transferring heat to the major walls;
(d) an electric blower;
(e) an electric heating element;
(f) means for guiding air from an outlet of the electric blower through the heating element and for guiding the heated air through the heat exchanging means;
(g) means for guiding chilled fluid from the pressure infusion device into the inlet of the fluid warming jacket, thereby causing the chilled fluid to be forced into the plurality of fluid conducting paths of the fluid warming jacket and causing the fluid warming paths to expand, thereby causing the fluid warming jacket to tightly contact the heated major walls of the recess, whereby fluid moving through the fluid conducting paths is heated;
(h) means for sensing the temperature of fluid near the outlet of the fluid warming jacket; and
(i) means for immediately controlling the temperature of the heating element in response to the sensed fluid temperature to rapidly correct any overtemperature condition in the blood,
whereby the low heat capacity of the guided, heated air is so low that corrections in the temperature of the heating element lead too immediate corresponding corrections in the temperature of the air and prevent temperature overshoot of the fluid as the fluid absorbs heat from the air during the temperature correction so that the temperature of the guided air can be increased to allow increased flow of the fluid without danger of overheating portions of the fluid.

21. The fluid warming apparatus of claim 20 wherein the fluid is blood.

22. The fluid warming apparatus of claim 21 including means for controlling the speed of the electric blower in response to the sensed blood temperature.

23. The fluid warming device of claim 21 including means for sensing the temperature of blood near the inlet of the blood sensing jacket and means for controlling the the temperature of the heating element in response to both the sensed inlet blood temperature and the sensed outlet blood temperature.

24. The fluid warming device of claim 21 including means for turning off the electric blower if the sensed blood outlet temperature exceeds a predetermined level.

25. The fluid warming device of claim 21 including means for turning off the electric blower and the electric heating element if the temperature of the blood exceeds a predetermined level.

26. The fluid warming device of claim 24 including means for turning off the heating element if the sensed outlet blood temperature exceeds a predetermined level.

27. The fluid warming device of claim 21 including a plurality of blood warming jackets and a plurality of the recesses for receiving the blood warming jackets, each of the recesses being bounded by closely spaced parallel major walls heated by transferring heat from the heated air to the heated major walls by the heat exchanging means.

28. The fluid warming device of claim 27 wherein each of the blood warming jackets is supported by a peripheral frame to facilitate insertion of the blood warming jacket into the recesses of the blood warming device.

29. The fluid warming device of claim 28 including means for operating on a signal produced by a temperature sensing element disposed in the blood warming jacket near the outlet thereof including an electronic control circuit producing first and second control signals and means for adjusting the temperature of the heating element in response to the first control signal and means for turning off the electric blower in response to the second control signal if the temperature of the outlet blood exceeds the predetermined level.

30. The fluid warming device of claim 29 including means for converting the signal representative of the sensed blood outlet temperature to a digital number by means of an analog-to-digital converter, a microprocessor operating to repetitively read the digital output of the analog-to-digital converter, and operate upon the digital output to produce heater control signals, and means for repetitively adjusting the heater temperature in response to the heater control signals.

31. The fluid warming device of claim 30 including means for operating the microprocessor in response to the digital output to generate blower speed control signals and means for repetitively adjusting the speed of the blower in response to the blower speed control signals.

32. The fluid warming device of claim 31 including means for operating the microprocessor to generate digital readout signals and producing a digital readout representative of the outlet blood temperature in response to the digital readout signals.

* * * * *